US008133668B2

(12) United States Patent
Kawaguchi

(10) Patent No.: US 8,133,668 B2
(45) Date of Patent: Mar. 13, 2012

(54) PROBE, PROBE SET, PROBE-IMMOBILIZED CARRIER, AND GENETIC TESTING METHOD

(75) Inventor: Masahiro Kawaguchi, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 165 days.

(21) Appl. No.: 12/295,274

(22) PCT Filed: Mar. 30, 2007

(86) PCT No.: PCT/JP2007/057717
§ 371 (c)(1),
(2), (4) Date: Aug. 10, 2009

(87) PCT Pub. No.: WO2007/114516
PCT Pub. Date: Oct. 11, 2007

(65) Prior Publication Data
US 2009/0305261 A1 Dec. 10, 2009

(30) Foreign Application Priority Data

Mar. 31, 2006 (JP) .................................. 2006-099497

(51) Int. Cl.
*C12Q 1/68* (2006.01)
*C12P 19/34* (2006.01)
*C07H 21/02* (2006.01)
*C07H 21/04* (2006.01)
(52) U.S. Cl. ........ 435/6; 435/91.2; 536/23.1; 536/24.32; 536/24.33
(58) Field of Classification Search .................. None
See application file for complete search history.

(56) References Cited

U.S. PATENT DOCUMENTS

| 5,474,796 | A | * | 12/1995 | Brennan ....................... 427/2.13 |
| 5,545,521 | A | | 8/1996 | Okamoto et al. |
| 5,624,798 | A | | 4/1997 | Yamamoto et al. |
| 5,670,315 | A | | 9/1997 | Yamamoto et al. |
| 5,705,346 | A | | 1/1998 | Okamoto et al. |
| 5,753,466 | A | | 5/1998 | Yano et al. |
| 5,939,256 | A | | 8/1999 | Yamamoto et al. |
| 6,395,533 | B1 | | 5/2002 | Kawaguchi et al. |
| 6,582,908 | B2 | * | 6/2003 | Fodor et al. ........................ 506/9 |
| 7,838,656 | B2 | * | 11/2010 | Yoshii et al. ................. 536/24.3 |
| 7,867,711 | B2 | * | 1/2011 | Yoshii et al. ...................... 435/6 |
| 7,943,313 | B2 | * | 5/2011 | Fukui et al. ................... 435/91.2 |
| 2004/0235032 | A1 | | 11/2004 | Suzuki et al. |
| 2004/0241643 | A1 | | 12/2004 | Yamamoto et al. |
| 2006/0046246 | A1 | * | 3/2006 | Zeng et al. ....................... 435/5 |
| 2008/0113364 | A1 | * | 5/2008 | Fukui et al. ....................... 435/6 |
| 2008/0113365 | A1 | * | 5/2008 | Kuribayashi et al. ............. 435/6 |
| 2008/0113366 | A1 | * | 5/2008 | Kuribayashi et al. ............. 435/6 |
| 2008/0124733 | A1 | * | 5/2008 | Fukui et al. ....................... 435/6 |
| 2009/0011413 | A1 | | 1/2009 | Ishii et al. |
| 2009/0130667 | A1 | * | 5/2009 | Fukui et al. ....................... 435/6 |
| 2009/0201220 | A1 | * | 8/2009 | Kim et al. ....................... 343/907 |
| 2009/0246775 | A1 | * | 10/2009 | Kuribayashi et al. ............. 435/6 |
| 2009/0298069 | A1 | * | 12/2009 | Fukui et al. ....................... 435/6 |
| 2009/0305262 | A1 | * | 12/2009 | Kuribayashi et al. ............. 435/6 |
| 2009/0305263 | A1 | * | 12/2009 | Fukui et al. ....................... 435/6 |
| 2009/0317809 | A1 | * | 12/2009 | Kuribayashi et al. ............. 435/6 |
| 2010/0081581 | A1 | * | 4/2010 | Fukui et al. ....................... 506/9 |
| 2010/0120028 | A1 | * | 5/2010 | Fukui et al. ....................... 435/6 |
| 2011/0003283 | A1 | * | 1/2011 | Kuribayashi et al. ............. 435/6 |

FOREIGN PATENT DOCUMENTS

| JP | 8-89254 | 4/1996 |
| JP | 2004-313181 | 11/2004 |
| JP | 2006-129810 | 5/2006 |

OTHER PUBLICATIONS

NCBI GenBank database, Accession No. DQ100448, Feb. 7, 2006.
NCBI GenBank database, Accession No. X73450, Jan. 9, 2004.
NCBI GenBank database, Accession No. AM040492, Mar. 8, 2006.
G. T. Attwood, et al., "Ammonia-Hyperproducing Bacteria from New Zealand Ruminants", Applied and Environmental Microbiology, vol. 64, No. 5, 1998, pp. 1796-1804.
F. E. Dewhirst, et al., "Characterization of novel human oral isolates and cloned 16S rDNA sequences that fall in the family *Coriobacteriaceae*: description of *Olsenella* gen. nov., reclassification of *Lactobacillus uli* as *Olsenella uli* comb. nov. and description of *Olsenella profusa* sp. nov."; International Journal of Systematic and Evolutionary Microbiology; vol. 51, 2001, pp. 1797-1804.
T. Garnier, et al., "Cloning, Mapping, and Molecular Characterization of the rRNA Operons of *Clostridium perfringens*", Journal of Bacteriology; vol. 173, No. 17, 1991, pp. 5431-5438.
R. Patel, et al., "Determination of 16S rRNA Sequences of *Enterococci* and Application to Species Identification of Nonmotile *Enterococcus gallinarum* Isolates"; vol. 36, No. 11, 1998, pp. 3399-3407.
B. J. Paster, et al., "Phylogeny of Bacteroides, *Prevotella*, and *Porphyromonas* spp. and Related Bacteria", Journal of Bacteriology, vol. 176, No. 3, 1994, pp. 725-732.
A. H. Smith, et al. "Effect of Condensed Tannins on Bacterial Diversity and Metabolic Activity in the Rat Gastrointestinal Tract", Applied and Environmental Microbiology; vol. 70, No. 2, 2004, pp. 1104-1115.
Y. Song, et al., "16S Ribosomal DNA Sequence-Based Analysis of Clinically Significant Gram-Positive Anaerobic *Cocci*", Journal of Clinical Microbiology; vol. 41, No. 4, 2003, pp. 1363-1369.
U.S. Appl. No. 12/264,241, International filing Date Jun. 23, 2003, Kawaguchi, et al.
U.S. Appl. No. 12/294,912, International Filing Date Mar. 30, 2007, Kawaguchi, et al.

(Continued)

*Primary Examiner* — Katherine Salmon
(74) *Attorney, Agent, or Firm* — Fitzpatrick, Cella, Harper & Scinto

(57) ABSTRACT

A nucleic acid probe for classification of pathogenic bacterial species is capable of collectively detecting bacterial strains of the same species and differentially detecting them from other bacterial species. Any one of the base sequences of SEQ ID NOS. 65 to 67 or a combination of at least two of them is used for detecting the gene of an infectious disease pathogenic bacterium.

13 Claims, 1 Drawing Sheet

OTHER PUBLICATIONS

PCT International Search Report and Written Opinion of the International Searching Authority in International Application No. PCT/JP2007/057717, Mailing Date May 29, 2007.
NCBI GenBank database, Accession No. AF542232, Apr. 14, 2003.
NCBI GenBank database, Accession No. AY319392, Feb. 9, 2004.
NCBI GenBank database, Accession No. AF292375, Nov. 16, 2001.
NCBI GenBank database, Accession No. AF044948, May 13, 1998.
NCBI GenBank database, Accession No. L16490, Jan. 29, 2001.
NCBI GenBank database, Accession No. L16492, Jan. 29, 2001.
NCBI GenBank database, Accession No. AF061008, Feb. 6, 1999.

* cited by examiner

FIG. 1

1st PCR PROTOCOL

| | |
|---|---|
| 95°C | 600sec |
| 92°C | 045sec ← |
| 72°C | 090sec ← 39CYCLE |
| 72°C | 600sec |
| 04°C or r.t. | HOLD |

FIG. 2

2nd PCR PROTOCOL

| | |
|---|---|
| 95°C | 600sec |
| 92°C | 045sec ← |
| 65°C | 045sec ← 24CYCLE |
| 72°C | 045sec ← |
| 72°C | 600sec |
| 04°C or r.t. | HOLD |

PROBE, PROBE SET, PROBE-IMMOBILIZED CARRIER, AND GENETIC TESTING METHOD

TECHNICAL FIELD

The present invention relates to a probe and a probe set for detecting a gene of infectious disease pathogenic bacterium, *Providencia rettgeri*, which are useful for detection and identification of the causative organism of an infectious disease, a probe-immobilized carrier on which the probe or the probe set is immobilized, a genetic testing method using the probe-immobilized carrier, and a genetic testing kit to be used for the method.

BACKGROUND ART

Heretofore, reagents for and methods of quickly and accurately detecting the causative organisms of infectious diseases in analytes have been proposed. For instance, Japanese Patent Application Laid-Open No. H08-89254 discloses oligonucleotides having specific base sequences, which can be respectively used as probes and primers for detecting pathogenic bacteria of candidiasis and aspergillosis, and a method of detecting target bacteria using such oligonucleotides. In addition, the same patent document also discloses a set of primers used for concurrently amplifying a plurality of target bacteria by PCR. In other words, those primers are used for the PCR amplification of nucleic acid fragments from fungi, which serve as a plurality of targets, in an analyte. The presence or absence of sequence portions, which are specific to the respective fungi, in the nucleic acid fragments amplified by the respective primers can be detected by a hybridization assay using probes specific to the respective fungi to identify fungal species in the analyte.

On the other hand, as a method capable of simultaneously detecting a plurality of oligonucleotides having different base sequences, there has been known a method using a probe array in which probes having sequences complementary to the respective base sequences are arranged at intervals on a solid support (Japanese Patent Application Laid-Open No. 2004-313181).

DISCLOSURE OF THE INVENTION

However, it is no easy task to establish a probe for specifically detecting a gene of an infectious disease pathogenic bacterium in a sample. That is, as well as the target gene, the sample may further contain genes of other infectious disease pathogenic bacteria. Thus, it is no easy task to establish the probe that specifically detects the gene of the infectious disease pathogenic bacterium while suppressing the influence of the presence of the genes of other infectious disease pathogenic bacteria (cross contamination). Under such circumstances, the inventors of the present invention have studied for obtaining a probe which allows accurate detection of a gene of an infectious disease pathogenic bacterium as mentioned hereinbelow while maintaining the cross contamination level low even when a sample in which genes of different bacteria are present is used. As a result, the inventors of the present invention have finally found a plurality of probes capable of precisely detecting the gene of the infectious disease pathogenic bacterium, *Providencia rettgeri*.

A first object of the present invention is to provide a probe and a probe set, which can precisely identify a gene of a target bacterium. Another object of the present invention is to provide a probe-immobilized carrier which can be used for precisely identifying a target bacterium from an analyte in which various bacteria are concurrently present. Still another object of the present invention is to provide a genetic testing method for detecting a target bacterium, which can quickly and precisely detect various bacteria in an analyte when they are present therein, and a kit for such a method.

The probe for detecting a gene of infectious disease pathogenic bacterium, *Providencia rettgeri*, of the present invention has any one of the following base sequences (1) to (4):

(1) CCTGGGAATGGCATCTAAGACTGGTCA (SEQ ID NO. 65)

or a complementary sequence thereof;

(2) GAGGAAGGCGTTGATGCTAATATCATCA (SEQ ID NO. 66)

or a complementary sequence thereof;

(3) GAGCAAAGCAGGGGAACTTCGGTC (SEQ ID NO. 67)

or a complementary sequence thereof; and (4) a modified sequence prepared such that any one of the sequences of SEQ ID NOS. 65 to 67 and the complementary sequences thereof is subjected to base deletion, substitution, or addition as far as the modified sequence retains a function as the probe.

In addition, the probe set for detecting a gene of infectious disease pathogenic bacterium, *Providencia rettgeri*, of the present invention includes at least two probes selected from the following items (A) to (L):

(A) a probe having a base sequence represented by

CCTGGGAATGGCATCTAAGACTGGTCA; (SEQ ID NO. 65)

(B) a probe having a base sequence represented by

GAGGAAGGCGTTGATGCTAATATCATCA; (SEQ ID NO. 66)

(C) a probe having a base sequence represented by

GAGCAAAGCAGGGGAACTTCGGTC; (SEQ ID NO. 67)

(D) a probe having a complementary sequence of the base sequence represented by SEQ ID NO. 65;

(E) a probe having a complementary sequence of the base sequence represented by SEQ ID NO. 66;

(F) a probe having a complementary sequence of the base sequence represented by SEQ ID NO. 67;

(G) a probe having a modified sequence obtained by base deletion, substitution, or addition on the base sequence represented by SEQ ID NO. 65 as far as it retains the function of a probe for detecting the gene of *Providencia rettgeri*;

(H) a probe having a modified sequence obtained by base deletion, substitution, or addition on the base sequence represented by SEQ ID NO. 66 as far as it retains the function of a probe for detecting the gene of *Providencia rettgeri*;

(I) a probe having a modified sequence obtained by base deletion, substitution, or addition on the base sequence represented by SEQ ID NO. 67 as far as it retains the function of a probe for detecting the gene of *Providencia rettgeri*;

(J) a probe having a modified sequence obtained by base deletion, substitution, or addition on the complementary sequence of the base sequence represented by SEQ ID NO. 65 as far as it retains the function of a probe for detecting the gene of *Providencia rettgeri*;

(K) a probe having a modified sequence obtained by base deletion, substitution, or addition on the complementary sequence of the base sequence represented by SEQ ID NO. 66 as far as it retains the function of a probe for detecting the gene of *Providencia rettgeri*; and (L) a probe having a modified sequence obtained by base deletion, substitution, or addition on the complementary sequence of the base sequence represented by SEQ ID NO. 67 as far as it retains the function of a probe for detecting the gene of *Providencia rettgeri*.

The characteristic feature of the probe-immobilized carrier of the present invention is that at least one of the above-mentioned probes (A) to (L) is immobilized on a solid-phase carrier, and when a plurality of probes are employed, the respective probes are arranged at intervals.

The method of detecting a gene of an infectious disease pathogenic bacterium in an analyte by using a probe-immobilized carrier of the present invention includes the steps of:

(i) reacting the analyte with the probe-immobilized carrier having the above-mentioned constitution; and (ii) detecting the presence or absence of a reaction of the probe on the probe-immobilized carrier with a nucleic acid in the analyte, or detecting the strength of a hybridization reaction of the probe on the probe-immobilized carrier with a nucleic acid in the analyte.

The characteristic feature of the kit for detecting an infectious disease pathogenic bacterium of the present invention is to include at least one of the above-mentioned probes (A) to (L), and a reagent for detecting a reaction between the probe with a target nucleic acid.

According to the present invention, when an analyte is infected with the above-mentioned causative bacterium, the bacterium can be more quickly and precisely identified from the analyte even if the analyte is simultaneously and complexly infected with other bacteria in addition to the above-mentioned bacterium. In particular, *Providencia rettgeri* can be detected while precisely distinguishing it from *Escherichia coli* which may otherwise cause cross contamination.

Further features of the present invention will become apparent from the following description of exemplary embodiments with reference to the attached drawings.

BRIEF DESCRIPTION OF THE DRAWINGS

FIG. 1 is a diagram illustrating a 1st PCR protocol.
FIG. 2 is a diagram illustrating a 2nd PCR protocol.

BEST MODE FOR CARRYING OUT THE INVENTION

The inventors of the present invention have obtained almost all of bacteria (represented by (1) to (62) below), which have been known as septicemia pathogenic bacteria so far, from the respective depository institutions and identified the 16S rRNA gene sequences of all the bacteria.

Subsequently, while making a comparison of all the identified sequences, probe sequences for *Providencia rettgeri* were investigated in detail and the probes of the present invention, which can identify *Providencia rettgeri*, have finally been found out.

| | | |
|---|---|---|
| (1) | *Staphylococcus aureus* | (ATCC12600) |
| (2) | *Staphylococcus epidermidis* | (ATCC14990) |
| (3) | *Escherichia coli* | (ATCC11775) |
| (4) | *Klebsiella pneumoniae* | (ATCC13883) |
| (5) | *Pseudomonas aeruginosa* | (ATCC10145) |
| (6) | *Serratia marcescens* | (ATCC13380) |
| (7) | *Streptococcus pneumoniae* | (ATCC33400) |
| (8) | *Haemophilus influenzae* | (ATCC33391) |
| (9) | *Enterobacter cloacae* | (ATCC13047) |
| (10) | *Enterococcus faecalis* | (ATCC19433) |
| (11) | *Staphylococcus haemolyticus* | (ATCC29970) |
| (12) | *Staphylococcus hominis* | (ATCC27844) |
| (13) | *Staphylococcus saprophyticus* | (ATCC15305) |
| (14) | *Streptococcus agalactiae* | (ATCC13813) |
| (15) | *Streptococcus mutans* | (ATCC25175) |
| (16) | *Streptococcus pyogenes* | (ATCC12344) |
| (17) | *Streptococcus sanguinis* | (ATCC10556) |
| (18) | *Enterococcus avium* | (JCM8722) |
| (19) | *Enterococcus faecium* | (ATCC19434) |
| (20) | *Pseudomonas fluorescens* | (ATCC13525) |
| (21) | *Pseudomonas putida* | (ATCC12633) |
| (22) | *Burkholderia cepacia* | (JCM5964) |
| (23) | *Stenotrophomonas maltophilia* | (ATCC13637) |
| (24) | *Acinetobacter baumannii* | (ATCC19606) |
| (25) | *Acinetobacter calcoaceticus* | (ATCC23055) |
| (26) | *Achromobacter xylosoxidans* | (ATCC27061) |
| (27) | *Vibrio vulnificus* | (ATCC27562) |
| (28) | *Salmonella choleraesuis* | (JCM1651) |
| (29) | *Citrobacter freundii* | (ATCC8090) |
| (30) | *Klebsiella oxytoca* | (ATCC13182) |
| (31) | *Enterobacter aerogenes* | (ATCC13048) |
| (32) | *Hafnia alvei* | (ATCC13337) |
| (33) | *Serratia liquefaciens* | (ATCC27592) |
| (34) | *Proteus mirabilis* | (ATCC29906) |
| (35) | *Proteus vulgaris* | (ATCC33420) |
| (36) | *Morganella morganii* | (ATCC25830) |
| (37) | *Providencia rettgeri* | (JCM1675) |
| (38) | *Aeromonas hydrophila* | (JCM1027) |
| (39) | *Aeromonas sobria* | (ATCC43979) |
| (40) | *Gardnerella vaginalis* | (ATCC14018) |
| (41) | *Corynebacterium diphtheriae* | (ATCC2701) |
| (42) | *Legionella pneumophila* | (ATCC33152) |
| (43) | *Bacillus cereus* | (ATCC14579) |
| (44) | *Bacillus subtilis* | (ATCC6051) |
| (45) | *Mycobacterium kansasii* | (ATCC12478) |
| (46) | *Mycobacterium intracellulare* | (ATCC13950) |
| (47) | *Mycobacterium chelonae* | (ATCC35752) |
| (48) | *Nocardia asteroids* | (ATCC19247) |
| (49) | *Bacteroides fragilis* | (JCM11019) |
| (50) | *Bacteroides thetaiotaomicron* | (JCM5827) |
| (51) | *Clostridium difficile* | (ATCC51695) |
| (52) | *Clostridium perfringens* | (JCM1290) |
| (53) | *Eggerthella lenta* | (JCM10763) |
| (54) | *Fusobacterium necrophorum* | (JCM3718) |
| (55) | *Fusobacterium nucleatum* | (ATCC25586) |
| (56) | *Lactobacillus acidophilus* | (ATCC4356) |
| (57) | *Anaerococcus prevotii* | (JCM6490) |
| (58) | *Peptoniphilus asaccharolyticus* | (JCM8143) |
| (59) | *Porphyromonas asaccharolytica* | (JCM6326) |
| (60) | *Porphyromonas gingivalis* | (JCM8525) |
| (61) | *Prevotella denticola* | (ATCC38184) |
| (62) | *Propionibacterium acnes* | (JCM6473) |

(The deposition numbers of the bacterial species obtained are shown in the respective parentheses on the right side in the above.)

The present invention provides an oligonucleotide probe for identifying an infectious disease pathogenic bacterium (hereinafter, simply referred to as a probe) and a probe set including a combination of two or more probes. The use of such a probe or a probe set allows the detection of the following bacterium which will cause inflammation by infection.

Bacterial Name

*Providencia rettgeri*

That is, the probe of the present invention can detect the 16S rRNA gene sequence among genes of the above-mentioned bacterium, having the following sequences:

(A) a probe having a base sequence represented by

```
                                        (SEQ ID NO. 65)
    CCTGGGAATGGCATCTAAGACTGGTCA;
```

(B) a probe having a base sequence represented by

```
                                        (SEQ ID NO. 66)
    GAGGAAGGCGTTGATGCTAATATCATCA;
```

(C) a probe having a base sequence represented by

```
                                        (SEQ ID NO. 67)
    GAGCAAAGCAGGGGAACTTCGGTC;
```

(D) a probe having a complementary sequence of the base sequence represented by SEQ ID NO. 65;

(E) a probe having a complementary sequence of the base sequence represented by SEQ ID NO. 66;

(F) a probe having a complementary sequence of the base sequence represented by SEQ ID NO. 67;

(G) a probe having a modified sequence obtained by base deletion, substitution, or addition on the base sequence represented by SEQ ID NO. 65 as far as it retains the function of a probe for detecting the gene of *Providencia rettgeri*;

(H) a probe having a modified sequence obtained by base deletion, substitution, or addition on the base sequence represented by SEQ ID NO. 66 as far as it retains the function of a probe for detecting the gene of *Providencia rettgeri*;

(I) a probe having a modified sequence obtained by base deletion, substitution, or addition on the base sequence represented by SEQ ID NO. 67 as far as it retains the function of a probe for detecting the gene of *Providencia rettgeri*;

(J) a probe having a modified sequence obtained by base deletion, substitution, or addition on the complementary sequence of the base sequence represented by SEQ ID NO. 65 as far as it retains the function of a probe for detecting the gene of *Providencia rettgeri*;

(K) a probe having a modified sequence obtained by base deletion, substitution, or addition on the complementary sequence of the base sequence represented by SEQ ID NO. 66 as far as it retains the function of a probe for detecting the gene of *Providencia rettgeri*; and (L) a probe having a modified sequence obtained by base deletion, substitution, or addition on the complementary sequence of the base sequence represented by SEQ ID NO. 67 as far as it retains the function of a probe for detecting the gene of *Providencia rettgeri*.

The probe set can be formed using at least two of those probes.

The above-mentioned modified sequences may include any variation as far as it does not impair the probe's function, or any variation as far as it hybridizes with a nucleic acid sequence of interest as a detection target. Above all, it is desirable to include any variation as far as it can hybridize with a nucleic acid sequence of interest as a detection target under stringent conditions. Preferable hybridization conditions confining the variation include those represented in examples as described below. Here, the term "detection target" used herein may be one included in a sample to be used in hybridization, which may be a unique base sequence to the infectious disease pathogenic bacterium, or may be a complementary sequence to the unique sequence. Further, the variation may be a modified sequence obtained by deletion, substitution, or addition of at least one base as far as it retains a function as the probe.

The functions of those probes significantly depend on the specificity of each probe sequence corresponding to the target nucleic acid sequence of interest. The specificity of a probe sequence can be evaluated from the degree of coincidence of bases with the target nucleic acid sequence and the melting temperature between the target nucleic acid sequence and the probe sequence. Further, when a plurality of probes constitute a probe set, the variance of melting temperatures among the probes may affect the performance of the probe set.

For designing a probe sequence, a region showing a high specificity to a specific bacterial species of interest regardless of any differences in strain is selected. The region contains three or more bases which are not coincident with corresponding bases in the sequences of any other bacterial species. The probe sequence is designed so that the melting temperature between the probe sequence and the corresponding sequence of the specific bacterial species of interest will differ by 10° C. or more from the melting temperatures between the probe sequence and the corresponding sequences of any other bacterial species. Further, one or more bases can be deleted or added so that the respective probes immobilized on a single carrier may have melting temperatures within a predetermined range.

The inventors of the present invention found out by experiments that the hybridization intensity of a probe will not be significantly attenuated if 80% or more of the base sequence is consecutively conserved. It can therefore be concluded, from the finding, such that any sequences modified from the probe sequences disclosed in the specification will have a sufficient probe function if 80% or more of the base sequence of the probe is consecutively conserved.

Those probe sequences are only specific to the DNA sequence coding for the 16S rRNA of the above-mentioned bacterium, so sufficient hybridization sensitivity to the sequence will be expected even under stringent conditions. In addition, any of those probe sequences forms a stable hybridized product through a hybridization reaction thereof with a target analyte even when the probe sequences are immobilized on a carrier, which is designed to produce an excellent result.

Further, a probe-immobilized carrier (e.g., DNA chip), on which the probe for detecting the infectious disease pathogenic bacterium of the present invention, can be obtained by supplying the probe on a predetermined position on the carrier and immobilizing the probe thereon. Various methods can be used for supplying the probe to the carrier. Among them, for example, a method, which can be suitably used, is to keep a surface state capable of immobilizing the probe on the carrier through a chemical bonding (e.g., covalent bonding) and a liquid containing the probe is then provided on a predetermined position by an inkjet method. Such a method allows the probe to be hardly detached from the carrier and exerts an additional effect of improving the sensitivity. In other words, when a stamping method conventionally used and called the Stanford method is employed to make a DNA chip, the resultant DNA chip has a disadvantage such that the applied DNA tends to be peeled off. Another one of the methods of forming DNA chips is to carry out the arrangement of probes by the synthesis of DNA on the surface of a carrier (e.g., DNA chip from Affymetrix Co., Ltd.). In such a method of synthesizing probes on a carrier, it is difficult to make equal the amount of synthesized DNA for each probe sequence. Thus, the amount of immobilized probe per immobilization area (spot) for each probe tends to vary considerably. Such variations in amounts of the respective immobilized probes may cause incorrect evaluation on the results of the detection with those probes. Based on this fact, the probe carrier of the present invention is preferably prepared using the above-mentioned inkjet method. The inkjet method as described above has an advantage such that the probe can be stably immobilized on the carrier and hardly detaching from the carrier to efficiently provide a probe carrier which can carry out detection with high sensitivity and high accuracy.

In addition, a probe set may include at least two selected from the group consisting of SEQ ID NOS. 65 to 67 as described above and the complementary sequences thereof and sequences obtained by base deletion, substitution, or addition on those sequences as far as they retain the function of a probe for detecting the gene of *Providencia rettgeri*. In this case, the accuracy of detecting the *Providencia rettgeri* gene can be further improved.

Hereinafter, preferred embodiments of the present invention will be described in detail.

Test objects to be tested using probe carriers (e.g., DNA chips) in which the probes of the present invention are immobilized on carriers include those originated from humans and animals such as domestic animals. For example, a test object is any of those which may contain bacteria, including: any body fluids such as blood, cerebrospinal fluid, expectorated sputum, gastric juice, vaginal discharge, and oral mucosal fluid; and excretions such as urine and feces. All media, which can be contaminated with bacteria, can be also subjected to a test using a DNA chip. Such media include: food, drink water and water in the natural environment such as hot spring water, which may cause food poisoning by contamination; filters of air cleaners and the like; and so on. Animals and plants, which should be quarantined in import/export, are also used as analytes of interest.

When the sample as described above can be directly used in reaction with the DNA chip, it is used as an analyte to react with the DNA chip and the result of the reaction is then analyzed. Alternatively, when the sample cannot be directly reacted with the DNA chip, the sample was subjected to extraction, purification, and other procedures for obtaining a target substance if required and then provided as an analyte to carry out a reaction with the DNA chip. For instance, when the sample contains a target nucleic acid, an extract, which may be assumed to contain such a target nucleic acid, is prepared from a sample, and then washed, diluted, or the like to obtain an analyte solution followed by reaction with the DNA chip. Further, as a target nucleic acid is included in an analyte obtained by carrying out various amplification procedures such as PCR amplification, the target nucleic acid may be amplified and then reacted with a DNA chip. Such analytes of amplified nucleic acids include the following ones:

(a) An amplified analyte prepared by using a PCR-reaction primer designed for detecting 16S rRNA gene.

(b) An amplified analyte prepared by an additional PCR reaction or the like from a PCR-amplified product.

(c) An analyte prepared by an amplification method other than PCR.

(d) An analyte labeled for visualization by any of various labeling methods.

Further, a carrier used for preparing a probe-immobilized carrier, such as a DNA chip, may be any of those that satisfy the property of carrying out a solid phase/liquid phase reaction of interest. Examples of the carrier include: flat substrates such as a glass substrate, a plastic substrate, and a silicon wafer; a three-dimensional structure having an irregular surface; and a spherical body such as a bead, and rod-, cord-, and thread-shaped structures. The surface of the carrier may be processed such that a probe can be immobilized thereon. Especially, a carrier prepared by introducing a functional group to its surface to enable chemical reaction has a preferable form from the viewpoint of reproducibility because the probe is stably bonded in the process of hybridization reaction.

Various methods can be employed for the immobilization of probes. An example of such a method is to use a combination of a maleimide group and a thiol (—SH) group. In this method, a thiol (—SH) group is bonded to the terminal of a probe, and a process is executed in advance to make the carrier (solid) surface have a maleimide group. Accordingly, the thiol group of the probe supplied to the carrier surface reacts with the maleimide group on the carrier surface to form a covalent bond, whereby the probe is immobilized.

Introduction of the maleimide group can utilize a process of firstly allowing a reaction between a glass substrate and an aminosilane coupling agent and then introducing an maleimide group onto the glass substrate by a reaction of the amino group with an EMCS reagent (N-(6-maleimidocaproyloxy) succinimide, available from Dojindo). Introduction of the thiol group to a DNA can be carried out using 5'-Thiol-Modifier C6 (available from Glen Research) when the DNA is synthesized by an automatic DNA synthesizer.

Instead of the above-described combination of a thiol group and a maleimide group, a combination of, e.g., an epoxy group (on the solid phase) and an amino group (nucleic acid probe terminal), can also be used as a combination of functional groups to be used for immobilization. Surface treatments using various kinds of silane coupling agents are also effective. A probe in which a functional group which can react with a functional group introduced by a silane coupling agent is introduced is used. A method of applying a resin having a functional group can also be used.

The detection of the gene of the infectious disease pathogenic bacterium by using the probe-immobilized carrier of the present invention can be carried out by a genetic testing method including the steps of:

(i) reacting an analyte with a probe-immobilized carrier on which the probe of the present invention is immobilized;

(ii) detecting the presence or absence of the reaction of a nucleic acid in the analyte with the probe on the probe-immobilized carrier, or detecting the strength of the reaction of a nucleic acid in the analyte with the probe on the probe-immobilized carrier; and (iii) specifying the probe having reacted with the nucleic acid in the analyte when the reaction of the probe with the nucleic acid in the analyte is detected and specifying the gene of the infectious disease pathogenic bacterium in the analyte based on the nucleic acid sequence of the probe.

The probe to be immobilized on the probe-immobilized carrier is at least one of the above-mentioned items (A) to (L). On the carrier, other probes (those for detecting bacterial species other than *Providencia rettgeri*) may be immobilized depending on the purpose of test. In this case, the other probes may be those capable of detecting the bacterial species other than *Providencia rettgeri* without causing cross contamination and the use of such probes allows simultaneous detection of a plurality of bacterial species with high accuracy.

Further, as described above, when the 16S rRNA gene sequence of an infectious disease pathogenic bacterium in the analyte is amplified by PCR and provided as a sample to be reacted with a probe carrier, a primer set for detecting the infectious disease pathogenic bacterium can be used. The primer set suitably includes at least one selected from oligonucleotides represented in the following items (1) to (21) and at least one selected from oligonucleotides represented in the following items (22) to (28), more suitably includes all the oligonucleotides represented in the following items (1) to (28):

(1) an oligonucleotide having a base sequence of

```
                                        (SEQ ID NO: 1);
5' gcggcgtgcctaatacatgcaag 3';
```

(2) an oligonucleotide having a base sequence of

```
                                        (SEQ ID NO: 2)
5' gcggcaggcctaacacatgcaag 3';
```

(3) an oligonucleotide having a base sequence of

```
                                        (SEQ ID NO: 3)
5' gcggcaggcttaacacatgcaag 3';
```

(4) an oligonucleotide having a base sequence of

```
                                        (SEQ ID NO: 4)
5' gcggtaggcctaacacatgcaag 3';
```

(5) an oligonucleotide having a base sequence of

```
                                        (SEQ ID NO: 5)
5' gcggcgtgcttaacacatgcaag 3';
```

(6) an oligonucleotide having a base sequence of

```
                                        (SEQ ID NO: 6)
5' gcgggatgccttacacatgcaag 3';
```

(7) an oligonucleotide having a base sequence of

```
                                        (SEQ ID NO: 7)
5' gcggcatgccttacacatgcaag 3';
```

(8) an ligonucleotide having a base sequence of

```
                                        (SEQ ID NO: 8)
5' gcggcatgcttaacacatgcaag 3';
```

(9) an oligonucleotide having a base sequence of

```
                                        (SEQ ID NO: 9)
5' gcggcgtgcttaatacatgcaag 3';
```

(10) an oligonucleotide having a base sequence of

```
                                        (SEQ ID NO: 10)
5' gcggcaggcctaatacatgcaag 3';
```

(11) an oligonucleotide having a base sequence of

```
                                        (SEQ ID NO: 11)
5' gcgggatgctttacacatgcaag 3';
```

(12) an oligonucleotide having a base sequence of

```
                                        (SEQ ID NO: 12)
5' gcggcgtgcctaacacatgcaag 3';
```

(13) an oligonucleotide having a base sequence of

```
                                        (SEQ ID NO: 13)
5' gcggcgtgcataacacatgcaag 3';
```

(14) an oligonucleotide having a base sequence of

5' gcggcatgcctaacacatgcaag 3';  (SEQ ID NO: 14)

(15) an oligonucleotide having a base sequence of

5' gcggcgcgcctaacacatgcaag 3';  (SEQ ID NO: 15)

(16) an oligonucleotide having a base sequence of

5' gcggcgcgcttaacacatgcaag 3';  (SEQ ID NO: 16)

(17) an oligonucleotide having a base sequence of

5' gcgtcatgcctaacacatgcaag 3';  (SEQ ID NO: 17)

(18) an oligonucleotide having a base sequence of

5' gcgataggcttaacacatgcaag 3';  (SEQ ID NO: 18)

(19) an oligonucleotide having a base sequence of

5' gcgacaggcttaacacatgcaag 3';  (SEQ ID NO: 19)

(20) an oligonucleotide having a base sequence of

5' gctacaggcttaacacatgcaag 3';  (SEQ ID NO: 20)

(21) an oligonucleotide having a base sequence of

5' acagaatgcttaacacatgcaag 3';  (SEQ ID NO: 21)

(22) an oligonucleotide having a base sequence of

5' atccagccgcaccttccgatac 3';  (SEQ ID NO: 22)

(23) an oligonucleotide having a base sequence of

5' atccaaccgcaggttcccctac 3';  (SEQ ID NO: 23)

(24) an oligonucleotide having a base sequence of

5' atccagccgcaggttcccctac 3';  (SEQ ID NO: 24)

(25) an oligonucleotide having a base sequence of

5' atccagccgcaccttccggtac 3';  (SEQ ID NO: 25)

(26) an oligonucleotide having a base sequence of

5' atccagcgccaggttccctag 3';   (SEQ ID NO: 26)

(27) an oligonucleotide having a base sequence of

5' atccagccgcaggttctcctac 3';   (SEQ ID NO: 27)

and
(28) an oligonucleotide having a base sequence of

5' atccagccgcacgttcccgtac 3'.   (SEQ ID NO: 28)

Among them, a primer designed for allowing the amplification of *Providencia rettgeri* is a primer set of the following:
(2) an oligonucleotide having a base sequence of 5' gcggcaggcctaacacatgcaag 3' (SEQ ID NO: 2); and at least one of
(23) an oligonucleotide having a base sequence of 5' atccaaccgcaggttcccctac 3'   (SEQ ID NO: 23)

and
(24) an oligonucleotide having a base sequence of

5' atccagccgcaggttcccctac 3'.   (SEQ ID NO: 24)

For detecting *Providencia rettgeri*, at least such a primer may be included.

The utilities of the respective primers (1) to (28) for amplification of *Providencia rettgeri* (JCM1675) can be evaluated and confirmed by comparing each sequence of SEQ ID NOS. 1 to 28 with a DNA sequence including the 16S rRNA coding region of *Providencia rettgeri* (SEQ ID NO. 68).

A kit for detecting the infectious disease pathogenic bacterium can be constructed using at least a probe as described above and a reagent for detecting a reaction of the probe with a nucleic acid in an analyte. The probe in the kit can preferably be provided as a probe-immobilized carrier as described above. Further, the detection reagent may contain a label to detect the reaction or a primer for carrying out amplification as a pre-treatment.

EXAMPLES

Hereinafter, the present invention will be described in more detail with reference to examples using probes for detecting an infectious disease pathogenic bacterium to detect *Providencia rettgeri*.

Example 1

In this example, microorganism detection using 2-step PCR will be described.

1. Preparation of Probe DNA

Nucleic acid sequences shown in Table 1 were designed as probes to be used for detection of *Providencia rettgeri*. Specifically, the following probe base sequences were selected from the genome part coding for the 16s rRNA gene of *Providencia rettgeri*. These probe base sequences were designed such that they could have an extremely high specificity to the bacterium, and a sufficient hybridization sensitivity could be expected without variance for the respective probe base sequences. The probe base sequences need not always completely match with those shown in Table 1. Probe base sequences having base lengths of 20 to 30, including the probe base sequences shown in Table 1, are also included in the probe base sequence shown in Table 1.

TABLE 1

| Name of micro-organism | Probe No. | SEQ ID NO. | Sequence |
|---|---|---|---|
| *Providencia rettgeri* | PR1 | 35 | 5' CCTGGGAATGGCATCTAAGACTGGTCA 3' |
| | PR2 | 36 | 5' GAGGAAGGCGTTGATGCTAATATCATCA 3' |
| | PR3 | 37 | 5' GAGCAAAGCAGGGGAACTTCGGTC 3' |

For each probe shown in Table 1, a thiol group was introduced, as a functional group to immobilize the probe on a DNA chip, to the 5' terminal of the nucleic acid after synthesis in accordance with a conventional method. After introduction of the functional group, purification and freeze-drying were executed. The freeze-dried probes for internal standard were stored in a freezer at −30° C.

2. Preparation of PCR Primers
2-1. Preparation of PCR Primers for Analyte Amplification As 16S rRNA gene (target gene) amplification PCR primers for pathogenic bacterium detection, nucleic acid sequences shown in Table 2 below were designed. Specifically, primer sets which specifically amplify the genome parts coding the 16S rRNAs, i.e., primers for which the specific melting points were made uniform as far as possible at the two end portions of the 16S rRNA coding region of a base length of 1,400 to 1,700 were designed. In order to simultaneously amplify a plurality of different bacterial species listed in the following items (1) to (62), mutants, or a plurality of 16S rRNA genes on genomes, a plurality of kinds of primers were designed. Note that a primer set is not limited to the primer sets shown in Table 2 as far as the primer set is available in common to amplify almost the entire lengths of the 16S rRNA genes of the pathogenic bacteria.

TABLE 2

| Primer No | SEQ ID NO. | Sequence |
|---|---|---|
| F01 | 1 | 5' GCGCCGTGCCTAATACATGCAAG 3' |
| F02 | 2 | 5' GCGGCAGGCCTAACACATGCAAG 3' |
| F03 | 3 | 5' GCGGCAGGCTTAACACATGCAAG 3' |
| F04 | 4 | 5' GCGGTAGGCCTAACACATGCAAG 3' |
| F05 | 5 | 5' GCGGCGTGCTTAACACATGCAAG 3' |
| F06 | 6 | 5' GCGGGATGCCTTACACATGCAAG 3' |
| F07 | 7 | 5' GCGGCATGCCTTACACATGCAAG 3' |
| F08 | 8 | 5' GCGGCATGCTTAACACATGCAAG 3' |
| F09 | 9 | 5' GCGGCGTGCTTAATACATGCAAG 3' |
| F10 | 10 | 5' GCGGCAGGCCTAATACATGCAAG 3' |
| F11 | 11 | 5' GCGGGATGCTTTACACATGCAAG 3' |
| F12 | 12 | 5' GCGGCGTGCCTAACACATGCAAG 3' |
| F13 | 13 | 5' GCGGCGTGCATAACACATGCAAG 3' |
| F14 | 14 | 5' GCGGCATGCCTAACACATGCAAG 3' |
| F15 | 15 | 5' GCGGCGCGCCTAACACATGCAAG 3' |

TABLE 2-continued

| Primer No | SEQ ID NO. | Sequence |
|---|---|---|
| F16 | 16 | 5' GCGGCGCGCTTAACACATGCAAG 3' |
| F17 | 17 | 5' GCGTCATGCCTAACACATGCAAG 3' |
| F18 | 18 | 5' GCGATAGGCTTAACACATGCAAG 3' |
| F19 | 19 | 5' GCGACAGGCTTAACACATGCAAG 3' |
| F20 | 20 | 5' GCTACAGGCTTAACACATGCAAG 3' |
| F21 | 21 | 5' ACAGAATGCTTAACACATGCAAG 3' |
| R01 | 22 | 5' ATCCAGCCGCACCTTCCGATAC 3' |
| R02 | 23 | 5' ATCCAACCGCAGGTTCCCCTAC 3' |
| R03 | 24 | 5' ATCCAGCCGCAGGTTCCCCTAC 3' |
| R04 | 25 | 5' ATCCAGCCGCACCTTCCGGTAC 3' |
| R05 | 26 | 5' ATCCAGCGCCAGGTTCCCCTAG 3' |
| R06 | 27 | 5' ATCCAGCCGCAGGTTCTCCTAC 3' |
| R07 | 28 | 5' ATCCAGCCGCACGTTCCCGTAC 3' |

(1) *Staphylococcus aureus*
(2) *Staphylococcus epidermidis*
(3) *Escherichia coli*
(4) *Klebsiella pneumoniae*
(5) *Pseudomonas aeruginosa*
(6) *Serratia marcescens*
(7) *Streptococcus pneumoniae*
(8) *Haemophilus influenzae*
(9) *Enterobacter cloacae*
(10) *Enterococcus faecalis*
(11) *Staphylococcus haemolyticus*
(12) *Staphylococcus hominis*
(13) *Staphylococcus saprophyticus*
(14) *Streptococcus agalactiae*
(15) *Streptococcus mutans*
(16) *Streptococcus pyogenes*
(17) *Streptococcus sanguinis*
(18) *Enterococcus avium*
(19) *Enterococcus faecium*
(20) *Pseudomonas fluorescens*
(21) *Pseudomonas putida*
(22) *Burkholderia cepacia*
(23) *Stenotrophomonas maltophilia*
(24) *Acinetobacter baumannii*
(25) *Acinetobacter calcoaceticus*
(26) *Achromobacter xylosoxidans*
(27) *Vibrio vulnificus*
(28) *Salmonella choleraesuis*
(29) *Citrobacter freundii*
(30) *Klebsiella oxytoca*
(31) *Enterobacter aerogenes*
(32) *Hafnia alvei*
(33) *Serratia liquefaciens*
(34) *Proteus mirabilis*
(35) *Proteus vulgaris*
(36) *Morganella morganii*
(37) *Providencia rettgeri*
(38) *Aeromonas hydrophila*
(39) *Aeromonas sobria*
(40) *Gardnerella vaginalis*
(41) *Corynebacterium diphtheriae*
(42) *Legionella pneumophila*
(43) *Bacillus cereus*
(44) *Bacillus subtilis*
(45) *Mycobacterium kansasii*
(46) *Mycobacterium intracellulare*
(47) *Mycobacterium chelonae*
(48) *Nocardia asteroides*
(49) *Bacteroides fragilis*
(50) *Bacteroides thetaiotaomicron*
(51) *Clostridium difficile*
(52) *Clostridium perfringens*
(53) *Eggerthella lenta*
(54) *Fusobacterium necrophorum*
(55) *Fusobacterium nucleatum*
(56) *Lactobacillus acidophilus*
(57) *Anaerococcus prevotii*
(58) *Peptoniphilus asaccharolyticus*
(59) *Porphyromonas asaccharolytica*
(60) *Porphyromonas gingivalis*
(61) *Prevotella denticola*
(62) *Propionibacterium acnes*

The primers shown in Table 2 were purified by high performance liquid chromatography (HPLC) after synthesis. The twenty-one forward primers and the seven reverse primers were mixed and dissolved in a TE buffer solution such that each primer concentration had an ultimate concentration of 10 pmol/μl.

2-2. Preparation of Labeling PCR Primers

In a manner similar to the above-mentioned analyte amplification primers, oligonucleotides having sequences as shown in Table 3 below were employed as primers for labeling.

TABLE 3

| Primer No | SEQ ID NO. | Sequence |
|---|---|---|
| Cy3R9-1 | 29 | 5' TACCTTGTTACGACTTCACCCCA 3' |
| Cy3R9-2 | 30 | 5' TACCTTGTTACGACTTCGTCCCA 3' |
| Cy3R9-3 | 31 | 5' TACCTTGTTACOACTTAGTCCCA 3' |
| Cy3R9-4 | 32 | 5' TACCTTGTTACGACTTAGCCCCA 3' |
| Cy3R9-5 | 33 | 5' TACCTTGTTACGACTTAGTCCTA 3' |
| Cy3R9-6 | 34 | 5' TACCTTGTTACGACTTAGCCCTA 3' |

The primers shown in Table 3 were labeled with a fluorescent dye, Cy3. The primers were purified by high performance liquid chromatography (HPLC) after synthesis. The six labeled primers were mixed and dissolved in a TE buffer solution such that each primer concentration had an ultimate concentration of 10 pmol/μl.

3. Extraction of Genome DNA (Model Analyte) of *Providencia rettgeri*

3-1. Microbial Culture & Genome DNA Extraction

First, *Providencia rettgeri* (JCM1675) was cultured in accordance with the conventional method. This microbial culture medium was subjected to the extraction and purification of genome DNA by using a nucleic acid purification kit (FastPrep FP100A FastDNA Kit, manufactured by Funakoshi Co., Ltd.).

3-2. Test of Collected Genome DNA

The collected genome DNA of the microorganism (*Providencia rettgeri*) was subjected to agarose electrophoresis and 260/280-nm absorbance determination in accordance with the conventional method. Thus, the quality (the admixture amount of low molecular nucleic acid and the degree of decomposition) and the collection amount were tested. In this example, about 10 μg of the genome DNA was collected. No degradation of genome DNA or contamination of rRNA was observed. The collected genome DNA was dissolved in a TE buffer solution at an ultimate concentration of 50 ng/μl and used in the following experiments.

4. Preparation of DNA Chip 4-1. Cleaning of Glass Substrate

A glass substrate (size: 25 mm×75 mm×1 mm, available from Iiyama Precision Glass) made of synthetic quartz was placed in a heat- and alkali-resisting rack and dipped in a cleaning solution for ultrasonic cleaning, which was adjusted to have a predetermined concentration. The glass substrate was kept dipped in the cleaning solution for a night and cleaned by ultrasonic cleaning for 20 min. The substrate was picked up, lightly rinsed with pure water, and cleaned by ultrasonic cleaning in ultrapure water for 20 min. The substrate was dipped in a 1N aqueous sodium hydroxide solution heated to 80° C. for 10 min. Pure water cleaning and ultrapure water cleaning were executed again. A quartz glass substrate for a DNA chip was thus prepared.

4-2. Surface Treatment

A silane coupling agent KBM-603 (available from Shin-Etsu Silicone) was dissolved in pure water at a concentration of 1% by weight (wt %) and stirred at room temperature for 2 hrs. The cleaned glass substrate was dipped in the aqueous solution of the silane coupling agent and left stand still at room temperature for 20 min. The glass substrate was picked up. The surface thereof was lightly rinsed with pure water and dried by spraying nitrogen gas to both surfaces of the substrate. The dried substrate was baked in an oven at 120° C. for 1 hr to complete the coupling agent treatment, whereby an amino group was introduced to the substrate surface. Next, N-maleimidocaproyloxy succinimido (abbreviated as EMCS hereinafter) was dissolved in a 1:1 (volume ratio) solvent mixture of dimethyl sulfoxide and ethanol to obtain an ultimate concentration of 0.3 mg/ml. As a result, an EMCS solution was prepared. Here, EMCS is N-(6-maleimidocaproyloxy)succinimido available from Dojindo.

The baked glass substrate was left stand and cooled and dipped in the prepared EMCS solution at room temperature for 2 hrs. By this treatment, the amino group introduced to the surface of the substrate by the silane coupling agent reacted with the succinimide group in the EMCS to introduce the maleimide group to the surface of the glass substrate. The glass substrate picked up from the EMCS solution was cleaned by using the above-described solvent mixture in which the EMCS was dissolved. The glass substrate was further cleaned by ethanol and dried in a nitrogen gas atmosphere.

4-3. Probe DNA

The microorganism detection probe prepared in the stage 1 (Preparation of Probe DNA) of Example 1 was dissolved in pure water. The solution was dispensed such that the ultimate concentration (at ink dissolution) became 10 μM. Then, the solution was freeze-dried to remove water.

4-4. DNA Discharge by BJ Printer and Bonding to Substrate

An aqueous solution containing 7.5-wt % glycerin, 7.5-wt % thiodiglycol, 7.5-wt % urea, and 1.0-wt % Acetylenol EH (available from Kawaken Fine Chemicals) was prepared. Each of the two probes (Table 1) prepared in advance was dissolved in the solvent mixture at a specific concentration. An ink tank for an inkjet printer (trade name: BJF-850, available from Canon) is filled with the resultant DNA solution and attached to the printhead.

The inkjet printer used here was modified in advance to allow printing on a flat plate. When a printing pattern is input in accordance with a predetermined file creation method, an about 5-picoliter of a DNA solution can be spotted at a pitch of about 120 μm.

The printing operation was executed for one glass substrate by using the modified inkjet printer to prepare an array. After confirming that printing was reliably executed, the glass substrate was left stand still in a humidified chamber for 30 min to make the maleimide group on the glass substrate surface react with the thiol group at the nucleic acid probe terminal.

4-5. Cleaning

After reaction for 30 min, the DNA solution remaining on the surface was cleaned by using a 10-mM phosphate buffer (pH 7.0) containing 100-mM NaCl, thereby obtaining a DNA chip in which single-stranded DNAs were immobilized on the glass substrate surface.

5. Amplification and Labeling of Analyte 5-1. Amplification of Analyte: 1st PCR

The amplification reaction (1st PCR) and the labeling reaction (2nd PCR) of a microbial gene to be provided as an analyte are shown in Table 4 below.

TABLE 4

| | |
|---|---|
| AmpliTaq Gold LD (5.0 U/μL) | 0.5 μL (2.5 unit/tube) |
| Primer mix <FR21x7> | 2.0 μL |
| Forward primer (x21 [0.625 μM/each]) | (final 1.25 pmol each/tube) |
| Reverse primer (x07 [1.875 μM/each]) | (final 3.75 pmol each/tube) |
| 10x PCR buffer | 5.0 μL (final 1x conc.) |
| $MgCl_2$ (25 mM) | 8.0 μL (final 4.0 mM) |
| dNTPmix (2.5 mM/each) | 4.0 μL (final 200 μM each) |
| Template | variable |
| $H_2O$ | up to 50 μL |
| Total | 50 μL |

Amplification reaction of the reaction solution having the above-mentioned composition was carried out using a commercially available thermal cycler in accordance with the protocol illustrated in FIG. 1. After the end of reaction, the primer was purified using a purification column (QIAquick PCR Purification Kit available from QIAGEN). Subsequently, the quantitative assay of the amplified product was carried out.

5-2. Labeling Reaction: 2nd PCR

Amplification reaction of the reaction solution having the composition shown in Table 5 was carried out using a commercially available thermal cycler in accordance with the protocol illustrated in FIG. 2.

TABLE 5

| | |
|---|---|
| Premix Taq (Ex Taq Version) | 25 μL |
| Cy3-labeled reverse primer mix | 0.83 μL |
| Cy3R9 mix (x06[10 μM/each]) | (final 8.3 pmol each/tube) |
| Template | variable (final 30 ng/tube) |
| $H_2O$ | up to 50 μL |
| Total | 50 μL |

After the end of reaction, the primer was purified using a purification column (QIAquick PCR Purification Kit available from QIAGEN) to obtain a labeled analyte.

6. Hybridization

Detection reaction was performed using the DNA chip prepared in the stage 4 (Preparation of DNA Chip) and the labeled analyte prepared in the stage 5 (Amplification and Labeling of Analyte).

6-1. Blocking of DNA Chip

Bovine serum albumin (BSA, Fraction V: available from Sigma) was dissolved in a 100-mM NaCl/10-mM phosphate buffer such that a 1 wt % solution was obtained. Then, the DNA chip prepared in the stage 4 (Preparation of DNA Chip) was dipped in the solution at room temperature for 2 hrs to execute blocking. After the end of blocking, the chip was cleaned using a washing solution as described below, rinsed with pure water and hydro-extracted by a spin dryer. The washing solution: 2×SSC solution (NaCl 300 mM, sodium citrate (trisodium citrate dihydrate, $C_6H_5Na_3.2H_2O$) 30 mM, pH 7.0) containing 0.1-wt % sodium dodecyl sulfate (SDS)

6-2. Hybridization

The hydro-extracted DNA chip was placed in a hybridization apparatus (Hybridization Station available from Genomic Solutions Inc). Hybridization reaction was carried out in a hybridization solution under conditions as described below.

6-3. Hybridization Solution

6×SSPE/10% formamide/target (all 2nd PCR products)/0.05 wt % (6×SSPE: NaCl 900 mM, $NaH_2PO_4H_2O$ 50 mM, EDTA 6 mM, pH, 7.4)

6-4. Hybridization Conditions

65° C. for 3 min, 55° C. for 4 hrs, washing with 2×SSC/0.1% SDS at 50° C., washing with 2×SSC/0.1% SDS at 20° C. (rinse with $H_2O$: manual), and spin dry.

7. Microorganism Genome Detection (Fluorometry)

The DNA chip after the end of hybridization reaction was subjected to fluorometry with a DNA chip fluorescent detector (GenePix 4000B available from Axon). As a result, *Providencia rettgeri* was able to be detected with a sufficient signal at a high reproducibility. The results of fluorometry are shown in Table 6 below.

TABLE 6

| Name of Probe | Fluorescence intensity | S/N |
|---|---|---|
| PR1 | 5024.7 | 109.7 |
| PR2 | 2273.9 | 49.7 |
| PR3 | 3484.7 | 76.1 |

8. Hybridization with Other Bacterial Species

For proving the fact that the probe sets shown in Table 1 can be specifically hybridized only with *Providencia rettgeri*, the results of hybridization reaction with *Escherichia coli* (JCM1649) are shown in Table 7 below.

TABLE 7

| Name of Probe | Fluorescence intensity | S/N |
|---|---|---|
| PR1 | 45.5 | 1.0 |
| PR2 | 46.7 | 1.0 |
| PR3 | 45.2 | 1.0 |

9. Results

As is evident from the above description, a DNA chip was prepared such that a probe set, which was able to detect only *Providencia rettgeri* in a specific manner, was immobilized. Further, the use of such a DNA chip allowed the identification of an infectious disease pathogenic bacterium, so the problems of the DNA probe derived from a microorganism was able to be solved. In other words, the oligonucleotide probe can be chemically produced in large amounts, while the purification or concentration thereof can be controlled. In addition, for classification of microbial species, a probe set capable of collectively detecting bacterial strains of the same species and differentially detecting them from bacteria of other species, was able to be provided.

Further, in addition to *Escherichia coli* as described above, hybridization reaction was carried out on each of nucleic acids extracted from the bacteria represented in the above-mentioned items (1) to (62). The results thereof confirmed that no substantial reaction was observed with respect to each of those bacteria in a manner similar to that of *Escherichia coli*, except of *Providencia rettgeri*.

The bacteria represented in the above-mentioned items (1) to (62) are pathogenic bacteria for septicemia, and they cover almost all of the pathogenic bacteria ever detected in human blood. Therefore, by using the primer of the present embodiment, the nucleic acid of an infectious disease pathogenic bacterium in blood can be extracted and then reacted with the probe of the present invention, whereby substantially accurate identification of *Providencia rettgeri* can be performed.

Further, according to the above-mentioned example, the presence of an infectious disease pathogenic bacterium can be efficiently determined with high accuracy by completely detecting the 16S rRNA gene from the gene of the infectious disease pathogenic bacterium.

Example 2

Preparation of DNA Chip by which Various Bacterial Species can be Simultaneously Determined In a manner similar to the stage 1 (Preparation of Probe DNA) of Example 1, probes having base sequences as shown in Table 8 below were prepared.

TABLE 8

| Bacterial species of interest | Probe sequence (5'→3') | SEQ ID NO. |
|---|---|---|
| Anaerococcus prevotii | TCATCTTGAGGTATGGAAGGGAAAGTGG | 35 |
|  | GTGTTAGGTGTCTGGAATAATCTGGGTG | 36 |
|  | ACCAAGTCTTGACATATTACGGCGG | 37 |
| Bacteroides fragilis | AAGGATTCCGGTAAAGGATGGGGATG | 38 |
|  | TGGAAACATGTCAGTGAGCAATCACC | 39 |
| Bacteroides thetaiotaomicron | AAGAATTTCGGTTATCGATGGGGATGC | 40 |
|  | AAGTTTTCCACGTGTGGAATTTTGTATGT | 41 |
|  | AAGGCAGCTACCTGGTGACAGGAT | 42 |
| Clostridium difficile | AATATCAAAGGTGAGCCAGTACAGGATGGA | 43 |
|  | CCGTAGTAAGCTCTTGAAACTGGGAGAC | 44 |
|  | TCCCAATGACATCTCCTTAATCGGAGAG | 45 |
| Clostridium perfringens | AACCAAAGGAGCAATCCGCTATGAGAT | 46 |
|  | GAGCGTAGGCGGATGATTAAGTGGG | 47 |
|  | CCCTTGCATTACTCTTAATCGAGGAAATC | 48 |
| Eggerthella lenta | GGAAAGCCCAGACGGCAAGGGA | 49 |
|  | CCTCTCAAGCGGGATCTCTAATCCGA | 50 |
|  | TGCCCCATGTTGCCAGCATTAGG | 51 |
| Fusobacterium necrophorum | TTTTCGCATGGAGGAATCATGAAAGCTA | 52 |
|  | AGATGCGCCGGTGCCCTTTCG | 53 |
|  | AGTCGGGAAGAAGTCAGTGACGGTAC | 54 |
| Peptoniphilus asaccharolyticus | GAGTACGTGCGCAAGCATGAAACT | 55 |
| Porphyromonas asaccharolytica | GAAGACTGCCCGCAAGGGTTGTAA | 56 |
|  | GTGTACTGGAGGTACGTGGAACGTG | 57 |
|  | GCATGAGGCTGAGAGGTCTCTTCC | 58 |

TABLE 8-continued

| Bacterial species of interest | Probe sequence (5'→3') | SEQ ID NO. |
|---|---|---|
| Porphyromonas gingivalis | TTATAGCTGTAAGATAGGCATGCGTCCC | 59 |
| | AACGGGCGATACGAGTATTGCATTGA | 60 |
| | ATATACCGTCAAGCTTCCACAGCGA | 61 |
| Enterococcus avium | TTTGAAAGGCGCTTTTGCGTCACTG | 62 |
| | CAAGGATGAGAGTAGAACGTTCATCCCTTG | 63 |
| | CAAGGATGAGAGTAGAATGTTCATCCCTTG | 64 |
| Providencia rettgeri | CCTGGGAATGGCATCTAAGACTGGTCA | 65 |
| | GAGGAAGGCGTTGATGCTAATATCATCA | 66 |
| | GAGCAAAGCAGGGGAACTTCGGTC | 67 |

Those probes are capable of specifically detecting certain bacterial species shown in the left column in the table just as one specific to *Providencia rettgeri* of Example 1.

Further, those probes are designed such that they have the same Tm value as that of a target, the same reactivity with a non-target sequence, and the like so that the nucleic acid of the bacterial species of interest can be specifically detected under the same reaction conditions.

For the respective probes, probe solutions were prepared in a manner similar to the stage 4-3 of Example 1. Subsequently, the inkjet printer used in the stage 4-4 of Example 1 was employed to discharge each of the probe solution on the same substrate to form a plurality of DNA chips having spots of the respective probes being arranged at a pitch of about 120 μm.

One of the DNA chips was used for hybridization with the nucleic acid extracted from *Providencia rettgeri* in a manner similar to the stage 6 of Example 1. As a result, the spot of the probe which specifically detected *Providencia rettgeri* showed almost the equal fluorescence intensity as that of Example 1. In contrast, the spots of other probes showed extremely low fluorescence intensity.

Further, other prepared DNA chips were used for hybridization with the bacteria listed in Table 8 except of *Providencia rettgeri*. As a result, the spot of *Providencia rettgeri* showed extremely low fluorescence intensity, while the spot of the probe for the bacterial species of interest showed extremely high fluorescence intensity. Therefore, the DNA chip prepared in the present example was confirmed that it was able to simultaneously determine eleven bacterial species listed in Table 8 in addition to *Providencia rettgeri*.

Example 3

Using the DNA chip prepared in Example 2, detection was attempted when a plurality of bacterial species was present in an analyte.

A culture medium in which *Providencia rettgeri* and *Clostridium difficile* were cultured was prepared and subjected to the same treatment as that of Example 1 to react with the DNA chip.

As a result, only the spots of the probes having SEQ ID NOS. 43, 44, 45, 65, 66, and 67 showed high fluorescence intensity, so the coexistence of those bacteria was able to be simultaneously confirmed.

The present invention is not limited to the above-mentioned embodiments and various changes and modifications can be made within the spirit and scope of the present invention. Therefore to apprise the public of the scope of the present invention, the following claims are made.

This application claims the benefit of Japanese Patent Application No. 2006-099497, filed Mar. 31, 2006, which is hereby incorporated by reference herein in its entirety.

The invention claimed is:

1. A probe set for detecting a gene of infectious disease pathogenic bacterium, *Providencia rettgeri*, comprising three probes consisting of the following base sequences (1) to (3) respectively:

(1) CCTGGGAATGGCATCTAAGACTGGTCA (SEQ ID NO. 65)

or the complementary sequence thereof;

(2) GAGGAAGGCGTTGATGCTAATATCATCA (SEQ ID NO. 66)

or the complementary sequence thereof; and (3) GAGCAAAGCAGGGGAACTTCGGTC (SEQ ID NO. 67)

or the complementary sequence thereof.

2. A probe-immobilized carrier, wherein the probe set of claim 1 is arranged on a solid-phase carrier.

3. A probe-immobilized carrier of claim 2, wherein the probe-immobilized carrier further comprises at least one probe having any one of the base sequences of SEQ ID NOS. 35 to 64 immobilized at a position spaced from the probe set.

4. A kit for detecting a gene of *Providencia rettgeri*, comprising:
   the probe set of claim 1; and
   a reagent for detecting a reaction between the probe set and a target nucleic acid.

5. A kit according to claim 4, wherein the reagent comprises a primer set for amplifying the gene of *Providencia rettgeri*, wherein the primer set comprises:
   an oligonucleotide comprising a base sequence of 5' gcggcaggcctaacacatgcaag 3';   (SEQ ID NO: 2)

and at least one of the oligonucleotides from the group consisting of:

an oligonucleotide comprising a base sequence of

5' atccaaccgcaggttcccctac 3'   (SEQ ID NO: 23)

and an oligonucleotide comprising a base sequence of

5' atccagccgcaggttcccctac 3'.   (SEQ ID NO: 24)

6. A gene detection kit, comprising: the probe-immobilized carrier of claim 3; and a reagent for detecting a reaction between the probe set and a target nucleic acid, wherein the reagent comprises a primer set, wherein the primer set comprises an oligonucleotide comprising a base sequence of 5' gcggcaggcctaacacatgcaag 3';   (SEQ ID NO: 2)

and at least one of the oligonucleotides from the group consisting of: an oligonucleotide comprising a base sequence of (SEQ ID NO: 23)
   5' atccaaccgcaggttcccctac 3';

and an oligonucleotide comprising a base sequence of (SEQ ID NO: 24)
   5' atccagccgcaggttcccctac 3'.

7. A probe set for detecting a gene of infectious disease pathogenic bacterium, *Providencia rettgeri*, comprising the following three probes (A) to (C), wherein the probe set does not comprise any other probes to detect the gene of *Providencia rettgeri*:

(A) a probe consisting of a base sequence represented by

CCTGGGAATGGCATCTAAGACTGGTCA; (SEQ ID NO. 65)

(B) a probe consisting of a base sequence represented by

GAGGAAGGCGTTGATGCTAATATCATCA; (SEQ ID NO. 66)

and (C) a probe consisting of a base sequence represented by

GAGCAAAGCAGGGGAACTTCGGTC. (SEQ ID NO. 67)

8. A probe-immobilized carrier, comprising the probe set of claim 7, wherein the three probes are arranged on a solid-phase carrier at intervals from each other.

9. A probe-immobilized carrier of claim 8, wherein the probe-immobilized carrier further comprises at least one probe having any one of the base sequences of SEQ ID NOS. 65 to 67 immobilized at a position spaced from the three probes.

10. A method of detecting a gene of *Providencia rettgeri* in an analyte by using a probe-immobilized carrier, comprising the steps of:

(i) reacting the analyte with the probe set on the probe-immobilized carrier of claim 2; and (ii) detecting the presence or absence of a hybridization reaction of the probe set on the probe-immobilized carrier with a nucleic acid in the analyte, or detecting the strength of a hybridization reaction of the probe set on the probe-immobilized carrier with the nucleic acid in the analyte, wherein the presence of the hybridization reaction or the strength of the hybridization reaction indicates the presence of a gene of *Providencia rettgeri* in the analyte.

11. A method according to claim 10, further comprising the step of carrying out PCR amplification of the nucleic acid in the analyte by using a primer set, wherein the primer set comprises:

an oligonucleotide comprising a base sequence of

5' gcggcaggcctaacacatgcaag 3'; (SEQ ID NO: 2)

and at least one of the oligonucleotides from the group consisting of: an oligonucleotide comprising a base sequence of 5' atccaaccgcaggttcccctac 3' (SEQ ID NO: 23)

and an oligonucleotide comprising a base sequence of

5' atccagccgcaggttcccctac 3'. (SEQ ID NO: 24)

12. A probe set according to claim 1, wherein the probe set shows a hybridization intensity weak enough to avoid cross-hybridization with the 16S rRNA coding region of any bacterium selected from *Anaerococcus prevotii, Bacteroides fragilis, Bacteroides thetaiotaomicron, Clostridium difficile, Clostridium perfringens, Eggerthella lenta, Fusobacterium necrophorum, Peptoniphilus asaccharolyticus, Porphyromonas asaccharolytica, Porphyromonas gingivalis* and *Enterococcus avium*.

13. A probe set according to claim 1, wherein the probe set shows a hybridization intensity weak enough to avoid cross-hybridization with the 16S rRNA coding region of any bacterium selected from *Staphylococcus aureus, Staphylococcus epidermidis, Escherichia coli, Klebsiella pneumoniae, Pseudomonas aeruginosa, Serratia marcescens, Streptococcus pneumoniae, Haemophilus influenzae, Enterobacter cloacae, Enterococcus faecalis, Staphylococcus haemolyticus, Staphylococcus hominis, Staphylococcus saprophyticus, Streptococcus agalactiae, Streptococcus mutans, Streptococcus pyogenes, Streptococcus sanguinis, Enterococcus avium, Enterococcus faecium, Pseudomonas fluorescens, Pseudomonas putida, Burkholderia cepacia, Stenotrophomonas maltophilia, Acinetobacter baumannii, Acinetobacter calcoaceticus, Achromobacter xylosoxidans, Vibrio vulnificus, Salmonella choleraesuis, Citrobacter freundii, Klebsiella oxytoca, Enterobacter aerogenes, Hafnia alvei, Serratia liquefaciens, Proteus mirabilis, Proteus vulgaris, Morganella morganii, Aeromonas hydrophila, Aeromonas sobria, Gardnerella vaginalis, Corynebacterium diphtheriae, Legionella pneumophila, Bacillus cereus, Bacillus subtilis, Mycobacterium kansasii, Mycobacterium intracellulare, Mycobacterium chelonae, Nocardia asteroids, Bacteroides fragilis, Bacteroides thetaiotaomicron, Clostridium difficile, Clostridium perfrigens, Eggerthella lenta, Fusobacterium necrophorum, Fusobacterium nucleatum, Lactobacillus acidophilus, Anaerococcus prevotii, Peptoniphilus asaccharolyticus, Porphyromonas asaccharolytica, Porphyromonas gingivalis, Prevotella denticola*, and *Propionibacterium acnes*.

\* \* \* \* \*

SEQUENCE LISTING

<160> NUMBER OF SEQ ID NOS: 68

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
gcggcgtgcc taatacatgc aag                                            23

<210> SEQ ID NO 2
<211> LENGTH: 23
<212> TYPE: DNA
<213> ORGANISM: Artificial Sequence
<220> FEATURE:
<223> OTHER INFORMATION: Primer

<400> SEQUENCE: 2
gcggcaggcc taacacatgc aag                                            23

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3

-continued gcggcaggct taacacatgc aag          23

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
gcggtaggcc taacacatgc aag          23

<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
gcggcgtgct taacacatgc aag          23

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
gcgggatgcc ttacacatgc aag          23

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
gcggcatgcc ttacacatgc aag          23

<210> SEQ ID NO 8
<211> LENGTH: 23
<212> TYPE: DNA
<213> ORGANISM: Artificial Sequence
<220> FEATURE:
<223> OTHER INFORMATION: Primer

<400> SEQUENCE: 8
gcggcatgct taacacatgc aag          23

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gcggcgtgct taatacatgc aag          23

<210> SEQ ID NO 10
<211> LENGTH: 23
<212> TYPE: DNA
<213> ORGANISM: Artificial Sequence

```
<220> FEATURE:
<223> OTHER INFORMATION: Primer

<400> SEQUENCE: 10
gcggcaggcc taatacatgc aag                                              23

<210> SEQ ID NO 11
<211> LENGTH: 23
<212> TYPE: DNA
<213> ORGANISM: Artificial Sequence
<220> FEATURE:
<223> OTHER INFORMATION: Primer

<400> SEQUENCE: 11
gcgggatgct ttacacatgc aag                                              23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
gcggcgtgcc taacacatgc aag                                              23

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
gcggcgtgca taacacatgc aag                                              23

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
gcggcatgcc taacacatgc aag                                              23

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
gcggcgcgcc taacacatgc aag                                              23

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
gcggcgcgct taacacatgc aag                                              23
```

```
<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gcgtcatgcc taacacatgc aag                                              23

<210> SEQ ID NO 18
<211> LENGTH: 23
<212> TYPE: DNA
<213> ORGANISM: Artificial Sequence
<220> FEATURE:
<223> OTHER INFORMATION: Primer

<400> SEQUENCE: 18
gcgataggct taacacatgc aag                                              23

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
gcgacaggct taacacatgc aag                                              23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
gctacaggct taacacatgc aag                                              23

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
acagaatgct taacacatgc aag                                              23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
atccagccgc accttccgat ac                                               22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
```
atccaaccgc aggttcccct ac                                                    22

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
atccagccgc aggttcccct ac                                                    22

<210> SEQ ID NO 25
<211> LENGTH: 22
<212> TYPE: DNA
<213> ORGANISM: Artificial Sequence
<220> FEATURE:
<223> OTHER INFORMATION: Primer

<400> SEQUENCE: 25
atccagccgc accttccggt ac                                                    22

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
atccagcgcc aggttcccct ag                                                    22

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
atccagccgc aggttctcct ac                                                    22

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
atccagccgc acgttcccgt ac                                                    22

<210> SEQ ID NO 29
<211> LENGTH: 23
<212> TYPE: DNA
<213> ORGANISM: Artificial Sequence
<220> FEATURE:
<223> OTHER INFORMATION: Primer

<400> SEQUENCE: 29
taccttgtta cgacttcacc cca                                                   23

<210> SEQ ID NO 30
<211> LENGTH: 23
<212> TYPE: DNA
<213> ORGANISM: Artificial Sequence

```
<220> FEATURE:
<223> OTHER INFORMATION: Primer

<400> SEQUENCE: 30
taccttgtta cgacttcgtc cca                                              23

<210> SEQ ID NO 31
<211> LENGTH: 23
<212> TYPE: DNA
<213> ORGANISM: Artificial Sequence
<220> FEATURE:
<223> OTHER INFORMATION: Primer

<400> SEQUENCE: 31
taccttgtta cgacttagtc cca                                              23

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
taccttgtta cgacttagcc cca                                              23

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
taccttgtta cgacttagtc cta                                              23

<210> SEQ ID NO 34
<211> LENGTH: 23
<212> TYPE: DNA
<213> ORGANISM: Artificial Sequence
<220> FEATURE:
<223> OTHER INFORMATION: Primer

<400> SEQUENCE: 34
taccttgtta cgacttagcc cta                                              23

<210> SEQ ID NO 35
<211> LENGTH: 28
<212> TYPE: DNA
<213> ORGANISM: Artificial
<220> FEATURE:
<223> OTHER INFORMATION: probe

<400> SEQUENCE: 35
tcatcttgag gtatggaagg gaaagtgg                                         28

<210> SEQ ID NO 36
<211> LENGTH: 28
<212> TYPE: DNA
<213> ORGANISM: artificial
<220> FEATURE:
<223> OTHER INFORMATION: probe

<400> SEQUENCE: 36
gtgttaggtg tctggaataa tctgggtg                                         28
```

```
<210> SEQ ID NO 37
<211> LENGTH: 25
<212> TYPE: DNA
<213> ORGANISM: artificial
<220> FEATURE:
<223> OTHER INFORMATION: probe

<400> SEQUENCE: 37
accaagtctt gacatattac ggcgg                                   25

<210> SEQ ID NO 38
<211> LENGTH: 26
<212> TYPE: DNA
<213> ORGANISM: artificial
<220> FEATURE:
<223> OTHER INFORMATION: probe

<400> SEQUENCE: 38
aaggattccg gtaaaggatg gggatg                                  26

<210> SEQ ID NO 39
<211> LENGTH: 26
<212> TYPE: DNA
<213> ORGANISM: artificial
<220> FEATURE:
<223> OTHER INFORMATION: probe

<400> SEQUENCE: 39
tggaaacatg tcagtgagca atcacc                                  26

<210> SEQ ID NO 40
<211> LENGTH: 27
<212> TYPE: DNA
<213> ORGANISM: artificial
<220> FEATURE:
<223> OTHER INFORMATION: probe

<400> SEQUENCE: 40
aagaatttcg gttatcgatg gggatgc                                 27

<210> SEQ ID NO 41
<211> LENGTH: 29
<212> TYPE: DNA
<213> ORGANISM: artificial
<220> FEATURE:
<223> OTHER INFORMATION: probe

<400> SEQUENCE: 41
aagttttcca cgtgtggaat tttgtatgt                               29

<210> SEQ ID NO 42
<211> LENGTH: 24
<212> TYPE: DNA
<213> ORGANISM: artificial
<220> FEATURE:
<223> OTHER INFORMATION: probe

<400> SEQUENCE: 42
aaggcagcta cctggtgaca ggat                                    24

<210> SEQ ID NO 43
<211> LENGTH: 30
<212> TYPE: DNA
<213> ORGANISM: artificial
<220> FEATURE:
<223> OTHER INFORMATION: probe

<400> SEQUENCE: 43
```
aatatcaaag gtgagccagt acaggatgga                                        30

<210> SEQ ID NO 44
<211> LENGTH: 28
<212> TYPE: DNA
<213> ORGANISM: artificial
<220> FEATURE:
<223> OTHER INFORMATION: probe

<400> SEQUENCE: 44
ccgtagtaag ctcttgaaac tgggagac                                          28

<210> SEQ ID NO 45
<211> LENGTH: 28
<212> TYPE: DNA
<213> ORGANISM: artificial
<220> FEATURE:
<223> OTHER INFORMATION: probe

<400> SEQUENCE: 45
tcccaatgac atctccttaa tcggagag                                          28

<210> SEQ ID NO 46
<211> LENGTH: 27
<212> TYPE: DNA
<213> ORGANISM: artificial
<220> FEATURE:
<223> OTHER INFORMATION: probe

<400> SEQUENCE: 46
aaccaaagga gcaatccgct atgagat                                           27

<210> SEQ ID NO 47
<211> LENGTH: 25
<212> TYPE: DNA
<213> ORGANISM: artificial
<220> FEATURE:
<223> OTHER INFORMATION: probe

<400> SEQUENCE: 47
gagcgtaggc ggatgattaa gtggg                                             25

<210> SEQ ID NO 48
<211> LENGTH: 29
<212> TYPE: DNA
<213> ORGANISM: artificial
<220> FEATURE:
<223> OTHER INFORMATION: probe

<400> SEQUENCE: 48
cccttgcatt actcttaatc gaggaaatc                                         29

<210> SEQ ID NO 49
<211> LENGTH: 22
<212> TYPE: DNA
<213> ORGANISM: artificial
<220> FEATURE:
<223> OTHER INFORMATION: probe

<400> SEQUENCE: 49
ggaaagccca gacggcaagg ga                                                22

<210> SEQ ID NO 50
<211> LENGTH: 26
<212> TYPE: DNA
<213> ORGANISM: artificial

```
<220> FEATURE:
<223> OTHER INFORMATION: probe

<400> SEQUENCE: 50
cctctcaagc gggatctcta atccga                                          26

<210> SEQ ID NO 51
<211> LENGTH: 23
<212> TYPE: DNA
<213> ORGANISM: artificial
<220> FEATURE:
<223> OTHER INFORMATION: probe

<400> SEQUENCE: 51
tgccccatgt tgccagcatt agg                                             23

<210> SEQ ID NO 52
<211> LENGTH: 28
<212> TYPE: DNA
<213> ORGANISM: artificial
<220> FEATURE:
<223> OTHER INFORMATION: probe

<400> SEQUENCE: 52
ttttcgcatg gaggaatcat gaaagcta                                        28

<210> SEQ ID NO 53
<211> LENGTH: 21
<212> TYPE: DNA
<213> ORGANISM: artificial
<220> FEATURE:
<223> OTHER INFORMATION: probe

<400> SEQUENCE: 53
agatgcgccg gtgcccttt c g                                              21

<210> SEQ ID NO 54
<211> LENGTH: 26
<212> TYPE: DNA
<213> ORGANISM: artificial
<220> FEATURE:
<223> OTHER INFORMATION: probe

<400> SEQUENCE: 54
agtcgggaag aagtcagtga cggtac                                          26

<210> SEQ ID NO 55
<211> LENGTH: 24
<212> TYPE: DNA
<213> ORGANISM: artificial
<220> FEATURE:
<223> OTHER INFORMATION: probe

<400> SEQUENCE: 55
gagtacgtgc gcaagcatga aact                                            24

<210> SEQ ID NO 56
<211> LENGTH: 24
<212> TYPE: DNA
<213> ORGANISM: artificial
<220> FEATURE:
<223> OTHER INFORMATION: probe

<400> SEQUENCE: 56
gaagactgcc cgcaagggtt gtaa                                            24
```

```
<210> SEQ ID NO 57
<211> LENGTH: 25
<212> TYPE: DNA
<213> ORGANISM: artificial
<220> FEATURE:
<223> OTHER INFORMATION: probe

<400> SEQUENCE: 57
gtgtactgga ggtacgtgga acgtg                                              25

<210> SEQ ID NO 58
<211> LENGTH: 24
<212> TYPE: DNA
<213> ORGANISM: artificial
<220> FEATURE:
<223> OTHER INFORMATION: probe

<400> SEQUENCE: 58
gcatgaggct gagaggtctc ttcc                                               24

<210> SEQ ID NO 59
<211> LENGTH: 28
<212> TYPE: DNA
<213> ORGANISM: artificial
<220> FEATURE:
<223> OTHER INFORMATION: probe

<400> SEQUENCE: 59
ttatagctgt aagataggca tgcgtccc                                           28

<210> SEQ ID NO 60
<211> LENGTH: 26
<212> TYPE: DNA
<213> ORGANISM: artificial
<220> FEATURE:
<223> OTHER INFORMATION: probe

<400> SEQUENCE: 60
aacgggcgat acgagtattg cattga                                             26

<210> SEQ ID NO 61
<211> LENGTH: 25
<212> TYPE: DNA
<213> ORGANISM: artificial
<220> FEATURE:
<223> OTHER INFORMATION: probe

<400> SEQUENCE: 61 ataccgtc aagcttccac agcga                                                25

<210> SEQ ID NO 62
<211> LENGTH: 25
<212> TYPE: DNA
<213> ORGANISM: artificial
<220> FEATURE:
<223> OTHER INFORMATION: probe

<400> SEQUENCE: 62
tttgaaaggc gcttttgcgt cactg                                              25

<210> SEQ ID NO 63
<211> LENGTH: 30
<212> TYPE: DNA
<213> ORGANISM: artificial
<220> FEATURE:
<223> OTHER INFORMATION: probe

<400> SEQUENCE: 63
```

-continued caaggatgag agtagaacgt tcatcccttg          30

<210> SEQ ID NO 64
<211> LENGTH: 30
<212> TYPE: DNA
<213> ORGANISM: artificial
<220> FEATURE:
<223> OTHER INFORMATION: probe

<400> SEQUENCE: 64
caaggatgag agtagaatgt tcatcccttg          30

<210> SEQ ID NO 65
<211> LENGTH: 27
<212> TYPE: DNA
<213> ORGANISM: artificial
<220> FEATURE:
<223> OTHER INFORMATION: probe

<400> SEQUENCE: 65
cctgggaatg gcatctaaga ctggtca             27

<210> SEQ ID NO 66
<211> LENGTH: 28
<212> TYPE: DNA
<213> ORGANISM: artificial
<220> FEATURE:
<223> OTHER INFORMATION: probe

<400> SEQUENCE: 66
gaggaaggcg ttgatgctaa tatcatca            28

<210> SEQ ID NO 67
<211> LENGTH: 24
<212> TYPE: DNA
<213> ORGANISM: artificial
<220> FEATURE:
<223> OTHER INFORMATION: probe

<400> SEQUENCE: 67
gagcaaagca ggggaacttc ggtc                24

<210> SEQ ID NO 68
<211> LENGTH: 1502
<212> TYPE: DNA
<213> ORGANISM: Providencia rettgeri

<400> SEQUENCE: 68
ctcagattga acgctggcgg caggcctaac acatgcaagt cgagcggtaa caggggaagc    60
ttgcttctcg ctgacgagcg gcggacgggt gagtaatgta tggggatctg cccgatagag   120
ggggataaact actggaaacg gtagctaata ccgcataatc tctyaggagc aaagcagggg   180
aacttcggtc cttgcgctat cggatgaacc catatggat tagctagtag gtgaggtaat    240
ggctcaccta gcgacgatc cctagctggt ctgagaggat gatcagccac actgggactg    300
agacacggcc cagactccta cgggaggcag cagtggggaa tattgcacaa tgggcgcaag   360
cctgatgcag ccatgccgcg tgtatgaaga aggccctagg gttgtaaagt actttcagtc   420
gggaggaagg cgttgatgct aatatcatca rcgattgacg ttaccgacag aagaagcacc   480
ggctaactcc gtgccagcag ccgcggtaat acggagggtg caagcgttaa tcggaattac   540
tgggcgtaaa gcgcacgcag gcggttgatt aagttagatg tgaaatcccc gggcttaacc   600
tgggaatggc atctaagact ggtcagctag agtcttgtag aggggggtag aattccatgt   660

```
gtagcggtga aatgcgtaga gatgtggagg aataccggtg gcgaaggcgg ccccctggac        720
aaagactgac gctcaggtgc gaaagcgtgg ggagcaaaca ggattagata ccctggtagt        780
ccacgctgta aacgatgtcg atttgaaggt tgttcccttg aggagtggct ttcggagcta        840
acgcgttaaa tcgaccgcct ggggagtacg gccgcaaggt taaaactcaa atgaattgac        900
gggggcccgc acaagcggtg gagcatgtgg tttaattcga tgcaacgcga agaaccttac        960
ctactcttga catccagaga ayttagcaga gatgctttrg tgccttcggg aactctgaga       1020
caggtgctgc atggctgtcg tcagctcgtg ttgtgaaatg ttgggttaag tcccgcaacg       1080
agcgcaaccc ttatcctttg ttgccagcga ttcggtcggg aactcaaagg agactgccgg       1140
tgataaaccg gaggaaggtg gggatgacgt caagtcatca tggcccttac gagtagggct       1200
acacacgtgc tacaatggcg tatacaaaga gaagcgacct cgcgagagca agcggaactc       1260
ataaagtacg tcgtagtccg gattggagtc tgcaactcga ctccatgaag tcggaatcgc       1320
tagtaatcgt agatcagaat gctacggtga atacgttccc gggccttgta cacaccgccc       1380
gtcacaccat gggagtgggt tgcaaaagaa gtaggtagct taaccttcgg gagggcgctt       1440
accactttgt gattcatgac tggggtgaag tcgtaacaag gtaaccgtag gggaacctgc       1500
gg                                                                     1502
```